US005465725A

United States Patent [19]

Seyed-Bolorforosh

[11] Patent Number: 5,465,725

[45] Date of Patent: Nov. 14, 1995

[54] ULTRASONIC PROBE

[75] Inventor: Mir S. Seyed-Bolorforosh, Palo Alto, Calif.

[73] Assignee: Hewlett Packard Company, Palo Alto, Calif.

[21] Appl. No.: 381,607

[22] Filed: Jan. 30, 1995

Related U.S. Application Data

[63] Continuation-in-part of Ser. No. 203,216, Feb. 28, 1994, Pat. No. 5,438,554, and a continuation-in-part of Ser. No. 319, 344, Oct. 6, 1994, Pat. No. 5,460,181, which is a continuation-in-part of Ser. No. 77,530, Jun. 15, 1993, Pat. No. 5,434,827.

[51] Int. Cl.[6] .......... A61B 8/00

[52] U.S. Cl. .......... 128/662.03; 310/366

[58] Field of Search .......... 128/660.01, 661.01, 128/662.03; 310/334, 359, 365, 366; 359/311; 73/625

[56] References Cited

U.S. PATENT DOCUMENTS

| | | | |
|---|---|---|---|
| 3,401,377 | 9/1968 | Bartlett | 340/173.2 |
| 3,462,746 | 8/1969 | Bartlett | 340/173.2 |
| 3,590,287 | 6/1971 | Berlincourt | 310/8.2 |
| 4,087,716 | 5/1978 | Heywang | 310/332 |
| 4,096,756 | 6/1978 | Alphonse | 73/609 |
| 4,129,799 | 12/1978 | Green | 73/625 |
| 4,296,348 | 10/1981 | Toda | 310/334 |
| 4,480,324 | 10/1984 | Sternberg | 367/150 |
| 4,516,838 | 5/1985 | Bademian | 359/311 |
| 4,939,826 | 7/1990 | Shoup | 29/25.35 |
| 5,025,790 | 6/1991 | Dias | 128/662.03 |
| 5,099,459 | 3/1992 | Smith | 367/153 |
| 5,175,709 | 12/1992 | Slayton et al. | 367/90 |
| 5,237,542 | 8/1993 | Burke et al. | 367/103 |
| 5,329,930 | 7/1994 | Thomas, III et al. | 128/661.01 |
| 5,371,717 | 12/1994 | Seyed-Bolorforosh | 367/140 |

FOREIGN PATENT DOCUMENTS

| | | | |
|---|---|---|---|
| 401027A2 | 12/1990 | European Pat. Off. | B06B 1/06 |
| 2059716 | 7/1983 | United Kingdom | H04R 17/00 |

OTHER PUBLICATIONS

R. E. Newman, D. P. Skinner, and L. E. Cross, "Connectivity and Piezoelectric–Pyroelectric Composites", Mat. Res. Bull., vol. 13, pp. 525–536, Pergamon Press, Inc.

N. Kim, S. J. Jang, and T. R. Shrout, "Relaxor Based Fine Grain Piezoelectric Materials", Proceedings of the 1990 IEEE International Symposium on Applications of Ferroelectrics; pp. 605–609, 1991.

W. Y. Pan. W. Y. Gu, D. J. Taylor, and L. E. Cross, "Large Piezoelectric Effect Induced by Direct Current Bias in PMN: PT Relaxor Ferroelectric Ceramics", Japanese Journal of Applied Physics, vol. 28, No. 4, Apr., 1989, pp. 653–661.

(List continued on next page.)

*Primary Examiner*—George Manuel

[57] ABSTRACT

A tunable ultrasonic probe of the that provides efficient electrical coupling of probe control lines to imaging system components and further provides for variable control over size of an effective acoustic aperture of the probe. The ultrasonic probe includes a body of a piezoelectric material that has a first surface and an opposing surface. A first set of electrodes is coupled with the first surface of the body. A second set of electrodes is also coupled with the first surface of the body and arranged so that each electrode of the second set substantially overlaps at least a respective one electrode of the first set. A third set of electrodes is coupled with the opposing surface of the body. At least one bias voltage source is coupled with the electrodes for substantially polarizing ceramic material within selected regions of the body. Switches are coupled with the first and second set of electrodes for changing an acoustic aperture of the probe by varying size of the selected polarized regions. The polarization of the selected regions of the piezoelectric material is controlled so as to variably tune a frequency of the beam of acoustic signals while controlling the acoustic aperture of the probe.

20 Claims, 14 Drawing Sheets

OTHER PUBLICATIONS

Thomas R. Shrout and Joseph Fielding, Jr., "Relaxor Ferroelectric Materials", 1990 Ultrasonic Symposium, 1990, IEEE, pp. 711–720.

Wallace Arden Smith, "New Opportunities in Ultrasonic Transducers Emerging from Innvoations In Piezoelectric Materials", SPIE, vo. 1733, 1992, pp. 3–26.

Wallace Arden Smith, "Modeling 1–3 Composite Piezoelectrics: Thickness–Mode Oscillations", IEEE Transactions on Ultrasonics, Piezoelectrics and Frequency Control, vol. 38, No. 1, Jan. 1991. pp. 40–48.

Hiroshi Takeuchi, Hiroshi Masazawa, Ohitose Makaya, and Yukio Ito, "Medical Ultrasonic Probe Using Electrostrictive–Cermics/Polymer Composite", 1989 Ultrasonics Symposium, 1989, IEEE, pp. 705–708.

Sixte de Fraguier, Jean–Francois Gelly, Leon Volnerman, and Olivier Lannuzel, "A Novel Acoustic Design for Dual Frequency Transducers Resulting in Separate Bandpass for Color Flow Mapping (CFM)".

D. J. Taylor, D. Damjanovic, A. S. Bhalla, and L. E. Cross, "Complex Piezoelectric, Elastic, and Dielectric Coefficients of La–Doped 0.93 $Pb(Mg_{1/3}Nb_{2/3})\ 0_3$:0.07 $PbTiO_3$ Under DC Bias", Ferroelectronics Letters, 1990, vol. 11, pp. 1–9.

D. J. Taylor, D. Damjanovic, A. S. Bhalla, and L. E. Cross, "Electric Field Dependence of $d_h$ In Lead Magnesium Niobate.Lead Titanate Ceramics", IEEE, 1991, pp. 341–345.

ULTRASONIC PROBE

CROSS REFERENCE TO RELATED APPLICATIONS

This is a continuation in part of application no. 8/203216entitled Tunable Acoustic Oscillator for Ultrasonic Transducers filed Feb. 28, 1994, now U.S. Pat. No. 5,438, 554 and of application Ser. No. 8/319344 entitled Ultrasonic Transducer for Three Dimensional Imaging filed Oct. 6, 1994, now U.S. Pat. No. 5,460,181 which is a continuation in part of application Ser. No. 08/077,530, filed Jun. 15, 1992, now U.S. Pat. No. 5,434,827.

FIELD OF THE INVENTION

This invention relates to ultrasonic transducers and, more particularly, to tunable ultrasonic transducers.

BACKGROUND OF THE INVENTION

Ultrasonic transducers are used in a wide variety of applications wherein it is desirable to view the interior of an object non-invasively. For example, in medical applications physicians use ultrasonic transducers to inspect the interior of a patient's body without making incisions or breaks in the patient's skin, thereby providing health and safety benefits to the patient. Accordingly, ultrasonic imaging equipment, including ultrasonic probes and associated image processing equipment, has found widespread medical use.

Ultrasonic probes provide a convenient and accurate way of gathering information about various structures of interest within a body being analyzed. In operation, ultrasonic probes generate a signal of acoustic waves that is acoustically coupled from the probe into the medium of the body so that the acoustic signal is transmitted into the body. As the acoustic signal propagates through the body, part of the signal is reflected by the various structures within the body and then received by the ultrasonic probe. By analyzing a relative temporal delay and intensity of the reflected acoustic waves received by the probe, a spaced relation of the various structures within the body and qualities related to acoustic impedance of the structures can be extrapolated from the reflected signal.

In operation, previously known medical probe generate a signal of acoustic waves using a plurality of piezoelectric elements. Despite the plurality of the piezoelectric elements, the elements are arranged proximate to one another so that the probe effectively has a single acoustic aperture integral with a top portion of the probe. The signal is acoustically coupled from the effective acoustic aperture of the probe into the medium of the patient's body, so that the signal is transmitted into the patient's body. Typically, this acoustic coupling is achieved by pressing the top portion of the probe into contact with a surface of the abdomen of the patient.

As the weakly reflected acoustic waves received by the probe propagate there through, they are electrically sensed by electrodes coupled to the probe. A large number of small probe electrodes are preferred to provide high resolution and control of a small, easy to handle, probe. Unfortunately, there are some difficulties in manufacturing the large number of small probe electrodes and in providing electrical coupling to the electrodes, because of the small size and complexity.

By analyzing a relative temporal delay and intensity of the weakly reflected waves received by the medical probe, imaging system components that are electrically coupled to the electrodes extrapolate an image from the weakly reflected waves to illustrate spaced relation of the various tissue structures within the patient's body.

Since the human body is not acoustically homogeneous, different frequencies of operation of an ultrasonic probe are desirable, depending upon which structures of the human body are serving as an acoustic transmission medium and which structures are the target to be imaged. Many commercially available ultrasonic probes include a transducer array that is optimized for use at only one particular acoustic frequency. Accordingly, when differing applications require the use of different ultrasonic frequencies, a user typically selects a probe which operates at or near a desired frequency from a collection of different probes. Complexity and cost of the ultrasonic imaging equipment is increased because a variety of probes, each having a different operating frequency, is needed. An economical and reliable alternative to manually coupling different transducers to such imaging systems is needed.

Previously known dual frequency ultrasonic probes utilize a transducer with a relatively broad resonance peak. Desired frequencies are selected by filtering. Current commercially available dual frequency probes typically have limited bandwidth ratios, such as 2.0/2.5 MHz or 2.7/3.5 MHz. Graded frequency ultrasonic sensors that compensate for frequency downshifting in the body are disclosed in U.S. Pat. No. 5,025,790, issued Jun. 25, 1991 to Dias. Dual frequency ultrasonic probes can additionally provide for added flexibility in "color flow" mapping wherein a first frequency is used for conventional echo-amplitude imaging and a second frequency is used for doppler shifted flow imaging.

While such previously known dual or graded frequency ultrasonic probes provide some advantages, variable control over size of the effective acoustic aperture of the probe is also needed. To maintain good image quality, it is desirable to maintain size of the effective acoustic aperture of the probe at a constant number of wavelengths of the acoustic signal. Accordingly, to maintain good and uniform image quality as frequency and therefore wavelength of the acoustic signal is varied, it is desirable to vary size of the acoustic aperture so that the size corresponds to a constant number of wavelengths of the signal. In the field of underwater sound transmitting or receiving systems used by the U.S. Navy at frequencies ranging from fifty to two hundred and fifty kilohertz, a stainless steel acoustic filter plate is used to provide an effective acoustic aperture diameter that is a constant multiple of the acoustic wavelength of the sound in the underwater medium, as explained in U.S. Pat. No. 4,480,324 issued to Sternberg. Because this patent provides helpful background information, it is incorporated herein by reference.

While the stainless steel filter plate provides some advantages, it has limited use in medical imaging applications because of its size, weight, and complexity and because medical imaging applications require operation at frequencies much higher than two hundred and fifty kilohertz operation of the plate. Since there is little equipment space available in hospital facilities, it is particularly important that the probe be compact.

What is needed is a tunable ultrasonic probe that provides efficient electrical coupling to imaging system components, while further providing variable control over size of the effective acoustic aperture of the probe.

SUMMARY OF THE INVENTION

A tunable ultrasonic probe of the present invention provides efficient electrical coupling of probe control lines to imaging system components and further provides for variable control over size of an effective acoustic aperture of the probe. Furthermore, the present invention is not limited by difficulties associated with manufacturing a large number of small electrodes as in previously known probes.

Briefly and in general terms, the ultrasonic probe of the invention includes a body of a piezoelectric material that has a first surface and an opposing surface. A first set of electrodes is coupled with the first surface of the body. A second set of electrodes is also coupled with the first surface of the body and arranged so that each electrode of the second set substantially overlaps at least a respective one electrode of the first set. A third set of electrodes is coupled with the opposing surface of the body. A principle of the invention is that since members of the first and second sets of electrodes overlap, the electrodes have an easily manufacturable size while retaining desired imaging resolution and control of the probe.

Preferably, the piezoelectric material includes a relaxor ferroelectric ceramic material having a variable polarization. At least one bias voltage source is coupled with the electrodes for substantially polarizing ceramic material within selected regions of the body. Switches are coupled with the first and second set of electrodes for changing an acoustic aperture of the probe by varying size of the selected polarized regions. Preferably, the switches are controlled so as to change the acoustic aperture of the probe in response to transmission of an acoustic beam from the probe and reception of the acoustic beam by the probe. The polarization of the selected regions of the piezoelectric material is controlled so as to variably tune a frequency of the beam of acoustic signals while controlling the acoustic aperture of the probe. In another preferred embodiment, switches are coupled with the first and second set of electrodes for apodizing the acoustic beam by varying size of the selected polarized regions.

In yet another preferred embodiment of the probe, the body of the piezoelectric material has a central axis and each member of the first and second sets of electrodes extend radially outward from the central axis of the body. Each member of the first and second set of electrodes is substantially sector shaped. The third set of electrodes coupled with the opposing surface of the body are concentrically arranged about the central axis of the body. Each member of the third set of electrodes is substantially semicircular. Such an arrangement provides an especially compact probe.

Other aspects and advantages of the present invention will become apparent from the following detailed description, taken in conjunction with the accompanying drawings, illustrating by way of example the principles of the invention.

DETAILED DESCRIPTION OF PREFERRED EMBODIMENT

Figure 1:
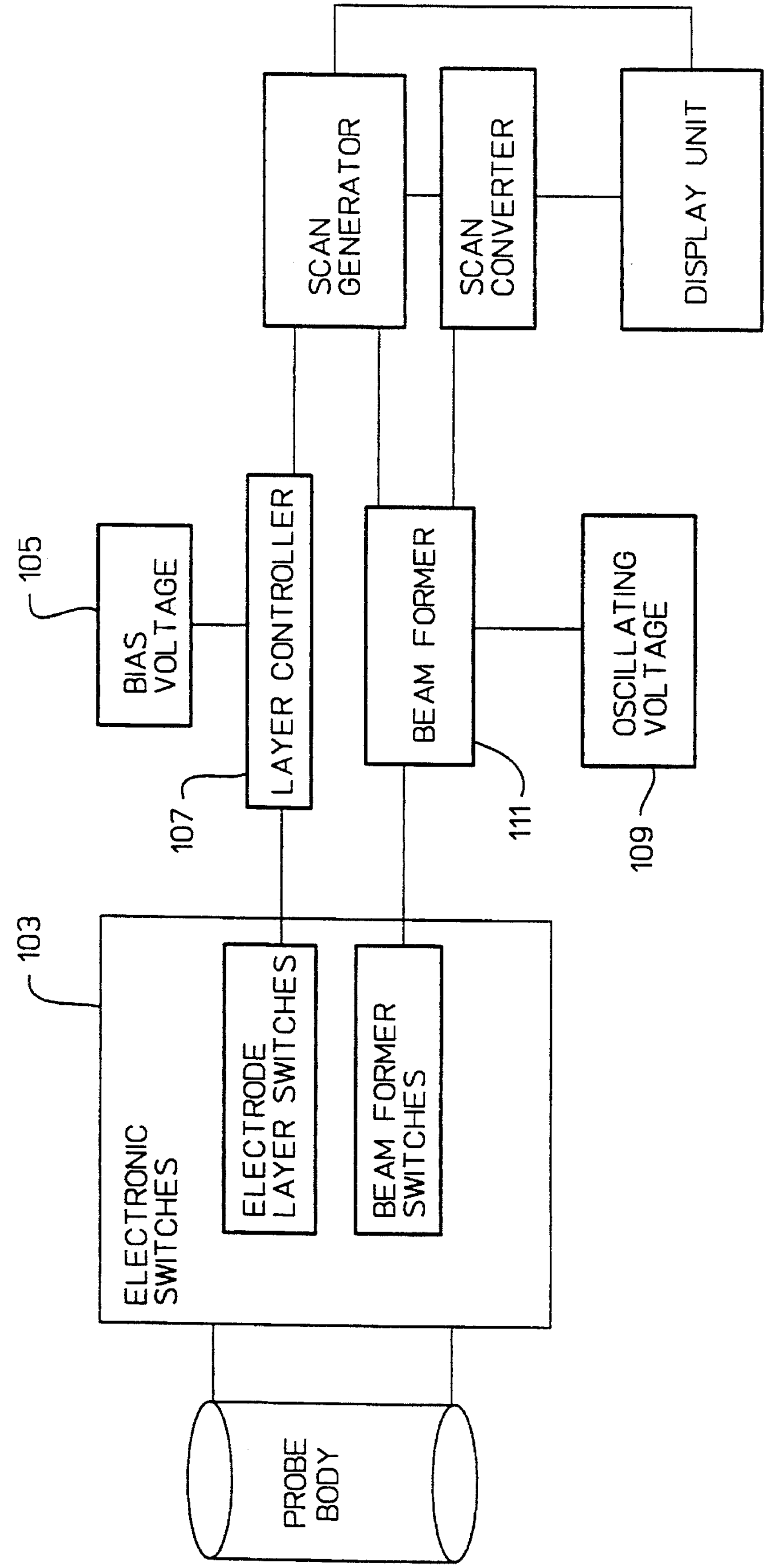
FIG. 1 is a schematic block diagram of the invention.

FIG. 1 is a block diagram of the invention. As schematically shown in FIG. 1, the invention includes a probe body 101. The body includes piezoelectric material, preferably a relaxor ferroelectric ceramic material. Preferably, the relaxor ferroelectric ceramic is a modified relaxor ferroelectric ceramic, doped to have a Curie temperature within a range of zero degrees Celsius to sixty degrees Celsius. Such doped relaxor ferroelectric ceramics are preferred because they advantageously provide a relatively high dielectric constant while providing a desirable Curie temperature that is near a typical room temperature of twenty five degrees Celsius. Accordingly, relaxor ferroelectric ceramics having a Curie temperature within a range of approximately 25 degrees Celsius to approximately 40 degrees Celsius are particularly desirable.

Various doped or "modified" relaxor ferroelectric ceramics are known, such as those discussed in "Relaxor Ferroelectric Materials" by Shrout et al., Proceedings of 1990 Ultrasonic Symposium, pp. 711–720, and in "Large Piezoelectric Effect Induced by Direct Current Bias in PMN; PT Relaxor Ferroelectric Ceramics" by Pan et al., Japanese Journal of Applied Physics, Vol. 28, No. 4, April 1989, pp. 653–661. Because these articles provide helpful supportive teachings, they are incorporated herein by reference. A doped or "modified" relaxor such as modified Lead Magnesium Niobate, $Pb(Mg_{1/3}Nb_{2/3})O_3$-$PbTiO_3$, also known as modified PMN or PMN-PT, is preferred. However, other relaxor ferroelectric ceramics such as Lead Lanthanum Zirconate Titanate, PLZT, may be used with beneficial results.

Figure 2:
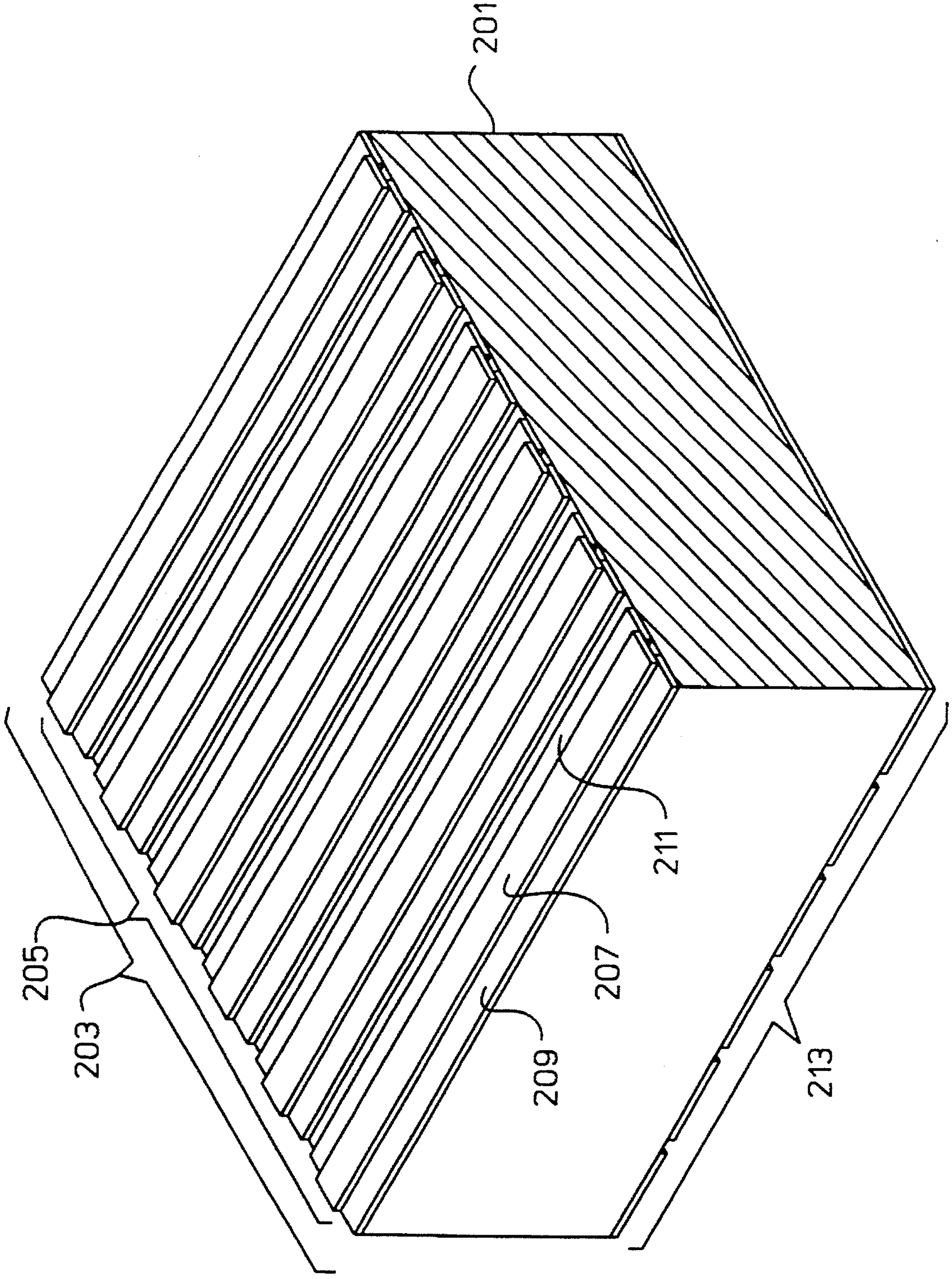
FIG. 2 is a simplified isometric view of a preferred embodiment of a probe body shown in FIG. 1.

FIG. 2 of the Shrout article is particularly helpful since it shows a phase diagram having a desired pseudo-cubic region for particular mole (x) PT concentrations and particular Curie temperatures of a $(1-x)Pb(Mg_{1/3}Nb_{2/3})O_3$-$(x)PbTiO_3)$ solid solution system. FIG. 8 of the Shrout article is also particularly helpful since it shows dielectric constant and Curie temperature of various alternative compositionally modified PMN ceramics. Among these alternatives, those doped with $Sc^{+3}$, $Zn^{+2}$, or $Cd^{+2}$ and having a Curie temperature within a range of approximately zero degrees Celsius to approximately sixty degrees Celsius are preferred.

Preferably, the body comprises a composite of the relaxor ferroelectric ceramic material and a filler material, such as polyethylene, for substantially acoustically isolating the selected regions from one another. While the relaxor ferroelectric ceramic material has a dielectric constant, preferably the filler material has a dielectric constant substantially lower than that of the ceramic material for substantially electrically isolating each of the selected regions from one another.

As will be discussed in further detail later herein, substantially planar electrodes are electrically coupled with the body. A first set of electrodes is coupled with the first surface of the body. A second set of electrodes is also coupled proximate with the first surface of the body and arranged so that each electrode of the second set substantially overlaps at least a respective one electrode of the first set. A third set of electrodes is coupled with the opposing surface of the body.

At least one bias voltage source is coupled with the electrodes for substantially polarizing ceramic material within selected regions of the body. Switches are coupled with the first and second set of electrodes through probe control lines for changing an acoustic aperture of the probe by varying size of the selected polarized regions. For example, as shown in FIG. 1 electronic switches 103 select electrodes so as to select column regions of the body that disposed between the electrodes and that are arranged adjacent to one another. The electronic switches include electrode layer switches as well as beam forming switches. A quasi-static (DC) bias voltage source 105 is coupled with the electronic switches for substantially polarizing ceramic material within the selected column regions of the body, while ceramic material in remainder regions of the body is substantially unpolarized and therefore substantially electromechanically inert. An electrode layer switch controller 107, preferably embodied in a suitably programmed microprocessor, dynamically configures the electronic switches to control bias applied to the first and second set of electrodes, so as to vary size of the selected polarized regions and so as to change an acoustic aperture of the probe.

An oscillating voltage source 109 that is tunable to a desired frequency excites the selected column regions to emit an acoustic beam having the desired frequency. A beam former 111 for variably phasing respective oscillating voltages is coupled with each of the selected regions so that the acoustic beam scans the medium. The beam former also provides electronic focussing of the acoustic beam at various depths, thereby providing both steering and focussing of the beam.

Operation of the layer controller and the beam former are co-ordinated by a scan generator, preferably embodied in the programmed microprocessor, coupled thereto as shown in FIG. 1. A scan converter including data memory blocks configured for storing three dimensional imaging data is coupled to the beam former and the scan generator. A display unit is coupled to the scan converter for displaying a high resolution acoustic image.

FIG. 2 is a simplified isometric view of a preferred embodiment of the probe body shown in FIG. 1. As shown, substantially planar electrodes are electrically coupled with the body of relaxor ferroelectric ceramic 201. A first set of spaced apart electrodes 203 is coupled with the first surface of the body. The members of the first set of electrodes are spaced apart from one another to provide a respective separation between each pair of adjacent members of the first set. A second set of electrodes 205 is also coupled proximate with the first surface of the body and arranged so that a respective member of the second set substantially overlaps the respective separation between each pair of adjacent members of the first set. For example, in the preferred embodiment shown in FIG. 2, a member 207 of the second set of electrodes substantially overlaps the separation between a first member 209 and an adjacent second member 211 of the first set of electrodes.

For ease of manufacturing, the second set of electrodes 205 is preferably arranged so that each electrode of the second set substantially overlaps at least a portion of a respective one electrode of the first set. For example, in the preferred embodiment shown in FIG. 2, a member 207 of the second set of electrodes substantially overlaps a portion of a first member 209 and a potion of a second member 211 of the first set of electrodes. Preferably a thin insulating polymer layer, for example Kaptan or Mylar film, is disposed between the first set of electrodes and the second set of electrodes. For the sake of simplicity, the thin insulating layer is not shown in the drawings.

A third set of electrodes 213 is coupled with the opposing surface of the body. Preferably, the third set of electrodes are arranged substantially perpendicular to the first and second set of electrodes as shown in FIG. 2, so as to advantageously control the acoustic aperture size in conjunction with the first and second set of electrodes. However beneficial results are also provided by alternative arrangements. For example, the third set of electrodes are alternatively arranged substantially parallel to the first and second set of electrodes so as to advantageously control undesired grating lobes of the acoustic beam in conjunction with the first and second set of electrodes. The electrodes preferably comprise a metal foil, such as copper foil, that is patterned using a series of photolithographic and adhesive bonding techniques to form the electrodes.

While electrodes of the invention are substantially planar, it should be understood that they need not be strictly flat since the electrodes in alternative embodiments of the invention have surfaces that are otherwise configured, for example as curved surfaces conforming to curved surfaces of the body of ferroelectric ceramic, provide beneficial results. Furthermore, it should be understood that while the preferred embodiment includes a larger number of electrodes than are shown in the figures, for the sake of simplicity, fewer electrodes are shown in the figures. For example, while for the sake of simplicity FIG. 2 shows twelve electrode members in the first set of electrodes 203, six electrode members in the second set of electrodes 205, and six electrode members in the third set of electrodes 213, it should be understood that an exemplary preferred embodiment includes a much larger number of electrodes, for example hundreds of electrodes.

Figure 3A:
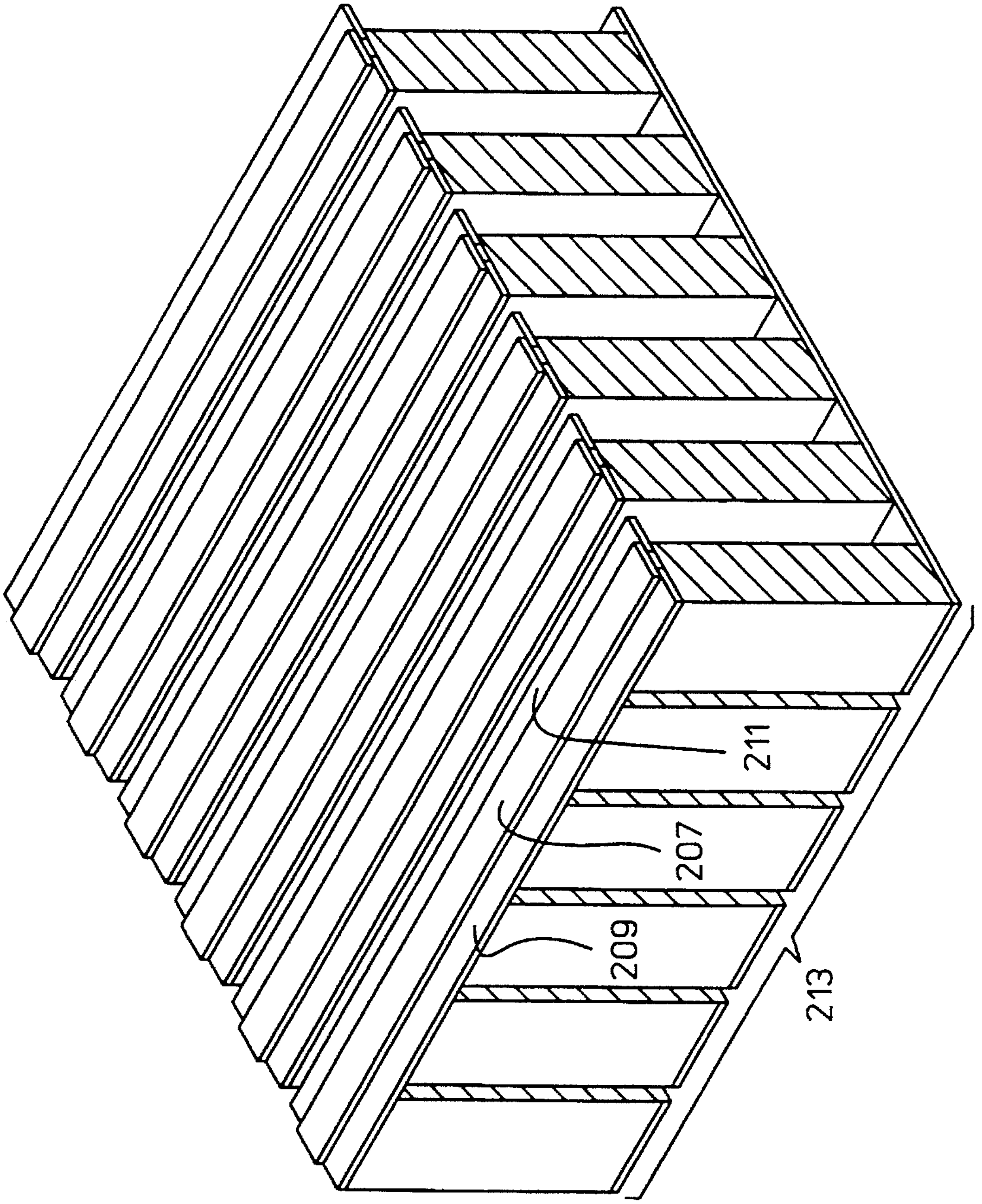
FIGS. 3A, 3B, and 3C are cut away views of the probe body shown in FIG. 2 illustrating operation of invention.
Figure 3B:
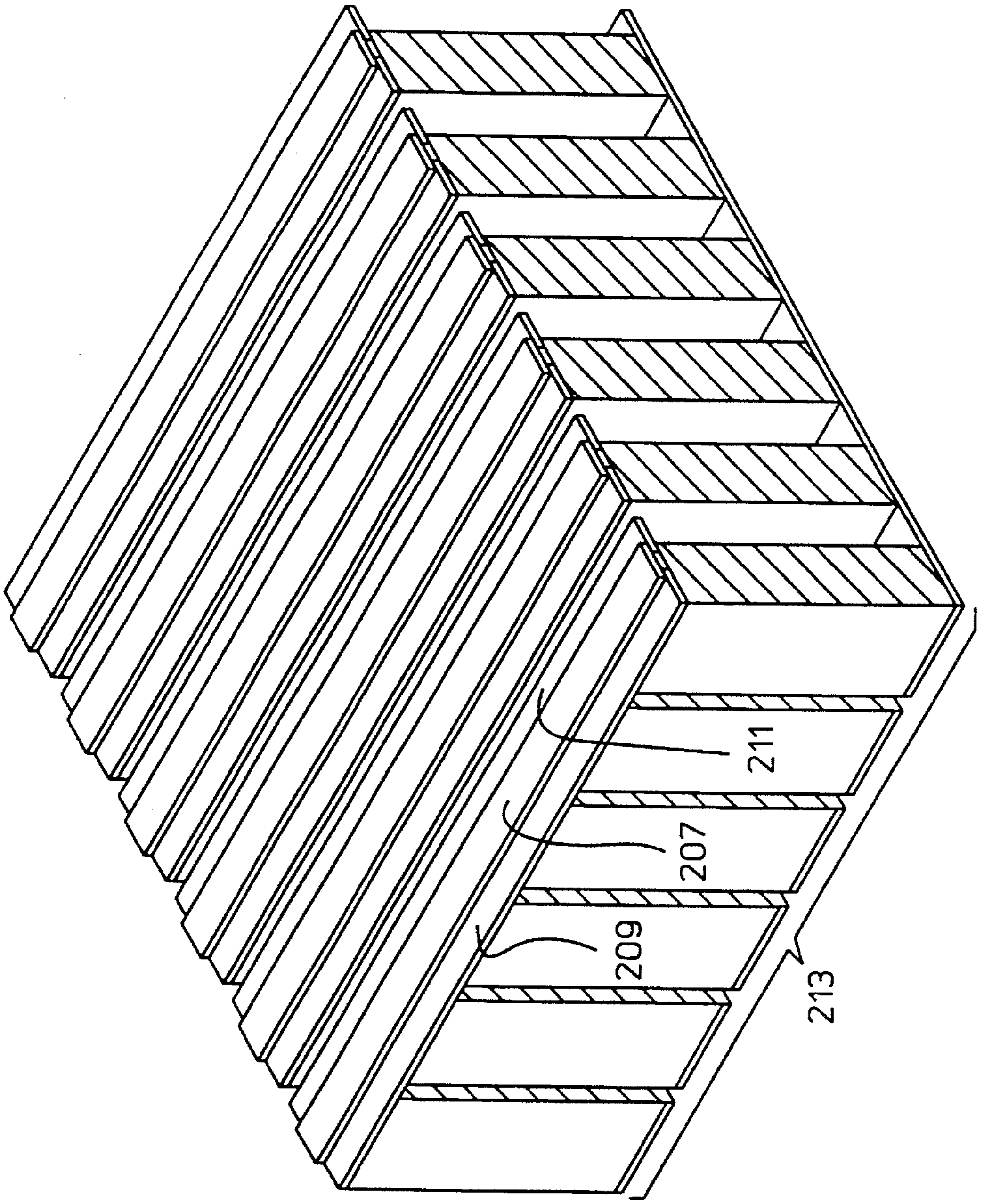
Figure 3C:
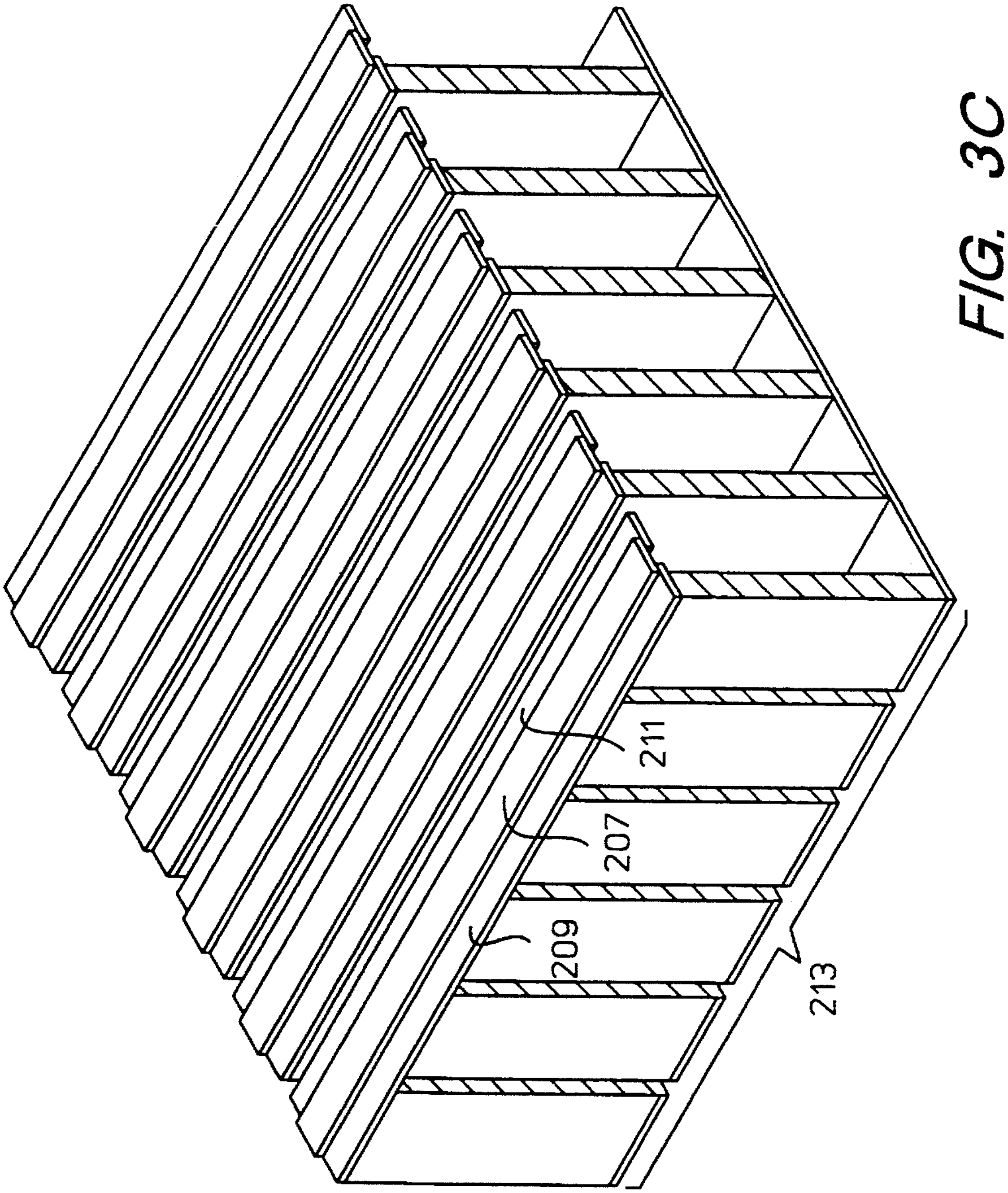

The relaxor ferroelectric ceramic material becomes polarized and therefore electromechanically active only under influence of the applied bias voltage. The present invention provides a large number of acoustic signal channels by using column regions of the body which are electrically selected by substantially polarizing the regions only when a bias voltage is applied to the regions by the novel electrode arrangement discussed previously herein and illustrated in FIG. 2. FIGS. 3A, 3B, and 3C are cut away views of the probe body shown in FIG. 2 illustrating operation of invention.

The electronic switches select all members of the first, second and third set of electrodes, so as to select column regions of the body that are arranged adjacent to one another as shown in FIG. 3A. The bias voltage source coupled with the electronic switches substantially polarizes ceramic material within the selected column regions of the body, while ceramic material in remainder regions of the body is substantially unpolarized. In FIGS. 3A, 3B and 3C the substantially unpolarized regions of the body are cut away to reveal the substantially polarized selected column regions.

The electrode layer switch controller dynamically configures the electronic switches for selectively coupling the bias voltage source to the first and second set of electrodes so as to vary size of the selected polarized regions, as illustrated by FIGS. 3A, 3B, and 3C. For example, for operation of the invention as in FIG. 3A, the third set of electrodes 213 is inductively grounded while the bias voltage source: is coupled through the switches, completing a circuit connection with the first and second members 209, 211 of the first set of electrodes and with the; member 207 of the second set of electrodes, thereby providing a first row of the polarized column regions as shown in FIG. 3A. Remaining members of the first and second set of electrodes are similarly configured to provide a remaining five rows of the polarized column regions as shown in FIG. 3A.

The tuned oscillating voltage source excites the selected column regions to emit an acoustic beam having the desired frequency. The beam former variably phases respective oscillating voltages coupled with each of the selected regions so that the acoustic beam scans a medium under examination by the probe. For the sake of simplicity, the medium under examination by the probe and the acoustic beam are not shown in the figures.

It should be understood that while an acoustic signal frequency is selected from among a range of acoustic signal frequencies by simply tuning the voltage source, in an alternative embodiment a relatively wider frequency range of acoustic signals is provided in accordance with teachings in application Ser No. 8/203216 entitled Tunable Acoustic Oscillator for Ultrasonic Transducers filed Feb. 28, 1994, which is incorporated herein by reference. In alternative embodiments one or more bodies of conventional piezoelectric material such as Lead Zirconate Titanate is acoustically coupled in series with the body of relaxor ferroelectric ceramic, and is electrically coupled in parallel with the body of relaxor ferroelectric by the electrodes. The conventional ceramic has a polarization that is fixed relative to the variable polarization of the relaxor ferroelectric ceramic. In the alternative embodiment, the bias voltage has a reversible electrical polarity for selecting one resonant frequency from a plurality of resonant frequencies of the probe. As another alternative, the bias voltage source has a variable voltage level for selecting at least one of a plurality of resonant frequencies of the probe.

It should also be understood that although a plurality of polarized column regions for generating the acoustic waves are shown in FIG. 3A, the polarized column regions are arranged proximate to one another to provide a single effective acoustic aperture integral with a top portion of the probe body. Size of the effective acoustic aperture is based upon size of the polarized column regions.

For FIG. 3B, members of the third set of electrodes 213 are once again inductively grounded while members of the second set of electrodes are once again coupled with the bias voltage source. However for FIG. 3B, alternating members of the first set of electrodes are alternatively biased by coupling to the bias voltage source and unbiased by being substantially disconnected from any bias voltage source. For example, the bias voltage source is coupled through the switches to the first member 209 of the first set of electrodes, while the second member 211 of the first set of electrodes is substantially disconnected from any bias voltage source. In this arrangement the member 207 of the second set of electrodes is also coupled with the bias voltage source, thereby providing a first row of the polarized column regions as shown in FIG. 3B. Similarly, members of the first and second set of electrodes are configured to provide a remaining five rows of the polarized column regions as shown in FIG. 3B.

As shown, substantially polarized ceramic material is disposed between grounded members of the third set of electrodes and biased members of the first set of electrodes. As additionally shown, substantially polarized ceramic material is disposed between grounded members of the third set of electrodes and where biased members of the second set of electrodes overlap the separation between the pairs of members of the first set of electrodes. Substantially unpolarized remainder regions of the ceramic are shown as cut away.

By comparing FIG. 3B to FIG. 3A, it is seen that the size of the polarized column regions in FIG. 3B is smaller than the size of the column regions in FIG. 3A. Accordingly, it should be understood that size of the effective acoustic aperture corresponding to the polarized column regions shown in FIG. 3B is smaller than the size of the effective acoustic aperture corresponding to the polarized column regions shown in FIG. 3A.

Size of the acoustic aperture is further varied by using the electrode layer switch controller to further vary size of the polarized column regions. For operation of the invention as in FIG. 3C, the third set of electrodes 213 is once again inductively grounded while alternating members of the first set of electrodes are alternatively biased by coupling to the bias voltage source and unbiased by being subtantially disconnected from any bias voltage source. For example, the bias voltage source is coupled through the switches to the first member 209 of the first set of electrodes, while the second member 211 of the first set of electrodes is substantially disconnected from any bias voltage source. However, for FIG. 3C the second set of electrodes is also unbiased by being substantially disconnected from any bias voltage, thereby providing a first row of the polarized column regions as shown in FIG. 3C. Similarly, members of the first and second set of electrodes are configured to provide a remaining five rows of the polarized column regions as shown in FIG. 3C. By comparing FIG. 3C to FIGS. 3A and 3C, it is seen that the size of the polarized column regions in FIG. 3C is smaller than the size of the column regions in FIGS. 3A and 3B. Accordingly, it should be understood that size of the effective acoustic aperture corresponding to the polarized column regions shown in FIG. 3B is smaller than the size of the effective acoustic apertures corresponding to the polarized column regions shown in FIGS. 3A and 3B.

To maintain imaging quality, it is desirable to maintain size of the effective acoustic aperture of the probe at a constant number of wavelengths of the acoustic signal. For example when the probe is operated at a first acoustic signal frequency, the effective acoustic aperture having the size based upon size of the polarized column regions as shown in FIG. 3A is selected so that size of the effective acoustic aperture of the probe corresponds to a substantially constant number of wavelengths of the acoustic signal. When the probe is operated at a second acoustic signal frequency higher than the first frequency, the effective acoustic aperture having the size based upon size of the polarized column regions as shown in FIG. 3B is selected so that size of the effective acoustic aperture of the probe still corresponds to the substantially constant number of wavelengths of the higher frequency acoustic signal. Similarly, when the probe is operated at a third acoustic signal frequency higher yet than the first and second frequencies, the effective acoustic aperture having the size based upon size of the polarized column regions as shown in FIG. 3C is selected so that size of the effective acoustic aperture of the probe once again corresponds to the substantially constant number of wavelengths of the yet higher frequency acoustic signal.

Figure 4:
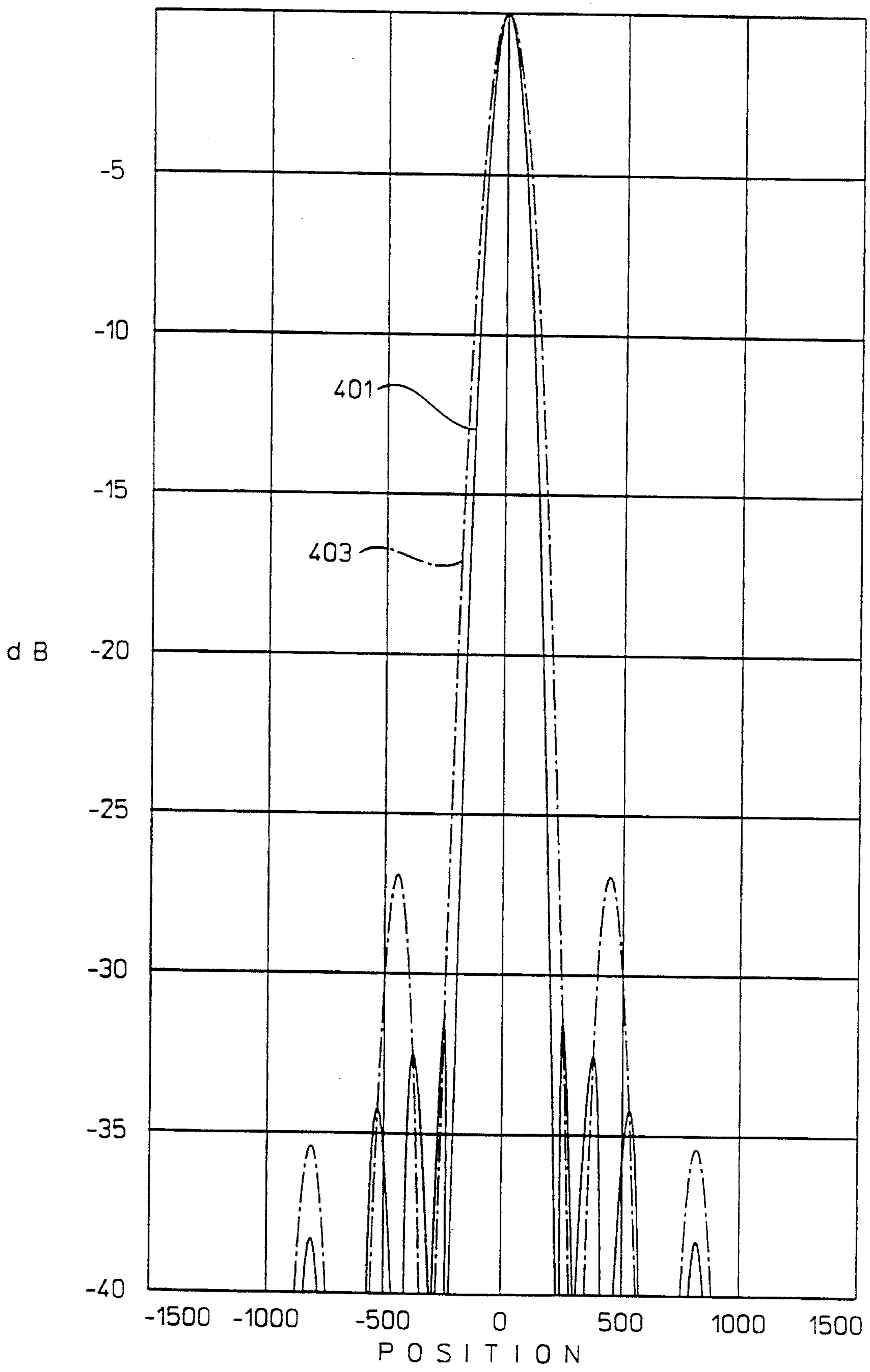
FIG. 4 shows a graph of a simulated two Way acoustic radiation pattern illustrating operation of the invention.

FIG. 4 shows a graph 401 of a simulated two way acoustic radiation, illustrating operation of the invention. In FIG. 4 a vertical axis is normalized amplitude in decibels (dB) and a horizontal axis is spacial position. The switches are controlled so as to change size of the acoustic aperture in response to transmission of an acoustic beam from the probe and reception of the acoustic beam by the probe. This advantageously provides a decrease in undesirable side lobes in the acoustic radiation pattern of the probe. For the sake of comparison, the acoustic aperture is maintained at the same size during both transmission and reception of the acoustic beam for another simulated radiation pattern graph 403 drawn in dotted line in FIG. 4. As shown, decreased side lobes are provided in the invention though adaptive beam forming techniques by transmitting the beam through an acoustic aperture having a first size and then receiving an echo of the beam through an acoustic aperture having a second size different than the first size. A beneficial decrease in side lobes is alternatively provided by operating the electrode layer switch controller to vary relative position of the polarized column regions, thus varying relative position of the corresponding effective acoustic aperture, in response to transmission of the acoustic beam from the probe and reception of the acoustic beam by the probe. As yet another alternative, side lobes are decrease by varying both size and position of the acoustic aperture in response to transmission of the acoustic beam from the probe and reception of the acoustic beam by the probe.

Figure 5:
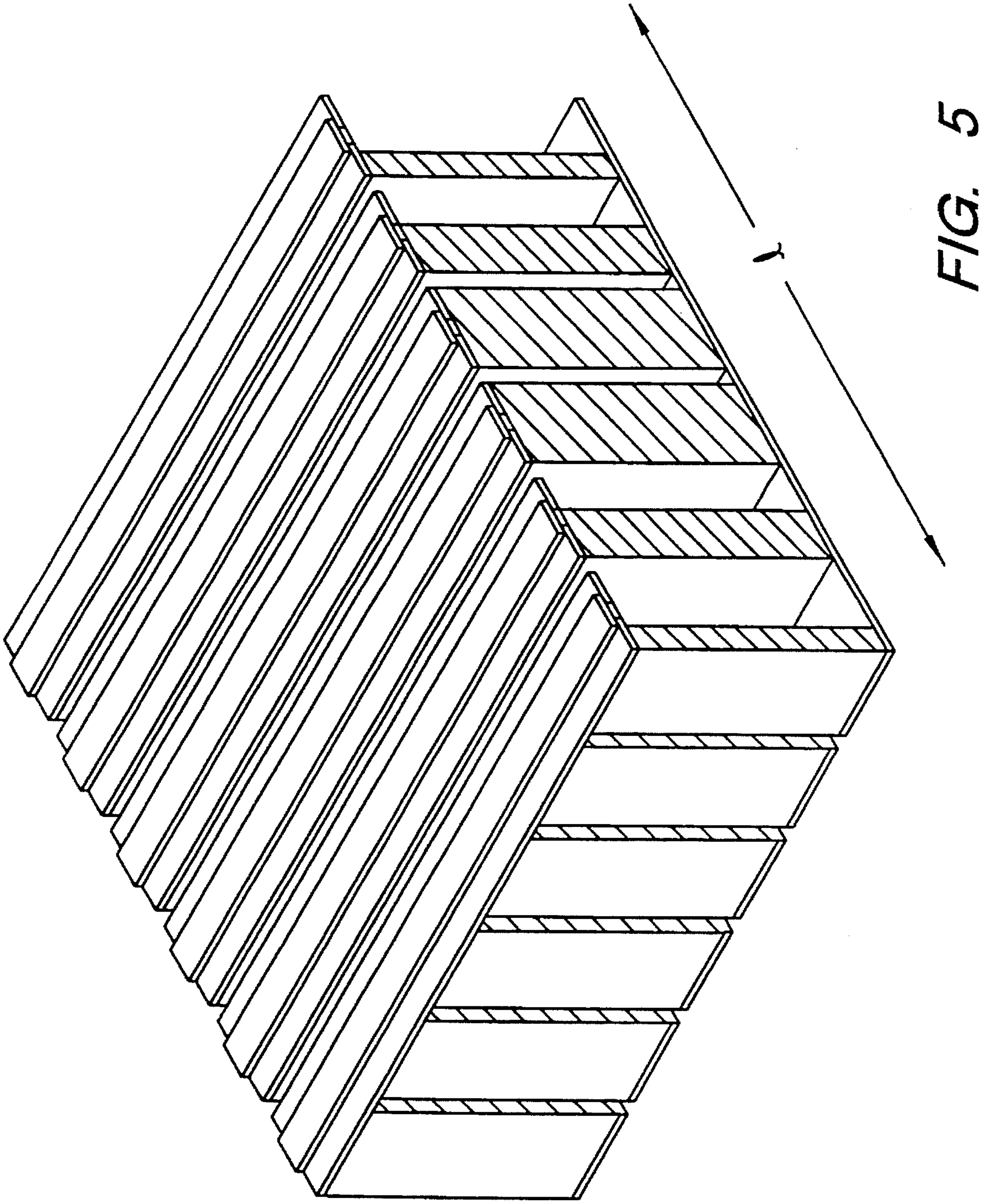
FIG. 5 is a cut away view illustrating operation of another preferred embodiment of the invention.

In another preferred embodiment of the invention, size of the selected polarized regions is varied along one or more dimensions of the relaxor ferroelectric ceramic body of the probe so as to apodize the acoustic beam. The electrode layer switch controller configures the electronic switches for selectively coupling the bias voltage source to the first and second set of electrodes in various combinations of that which is described previously herein with respect to FIGS. 3A, 3B, and 3C. For example, FIG. 5 is a cut away view of the probe body showing size of the selected polarized regions varied along a longitudinal dimension, I, of the probe body so as to apodize the acoustic beam. In FIG. 5 substantially unpolarized regions of the body are cut away to reveal the substantially polarized selected column regions.

In yet another preferred embodiment of the probe shown in various views is FIGS. 6A through 6D, the body of the piezoelectric material 601 of the probe has a central axis 602 and each member of a first set of electrodes 603 and second set of electrodes 605 substantially overlap and extend radially outward from the central axis of the body. As shown, each member of the first and second set of electrodes is substantially sector shaped. The third set of electrodes 613 is coupled with an opposing surface of the body are concentrically arranged about the central axis of the body. As shown each member of the third set of electrodes is substantially semicircular. A preferred method and apparatus for scanning the probe shown in FIGS. 6A through 6D is taught in application Ser. No. 8/319344 entitled Ultrasonic Transducer for Three Dimensional Imaging filed Oct. 6, 1994, which is incorporated herein by reference.

Figure 6A:
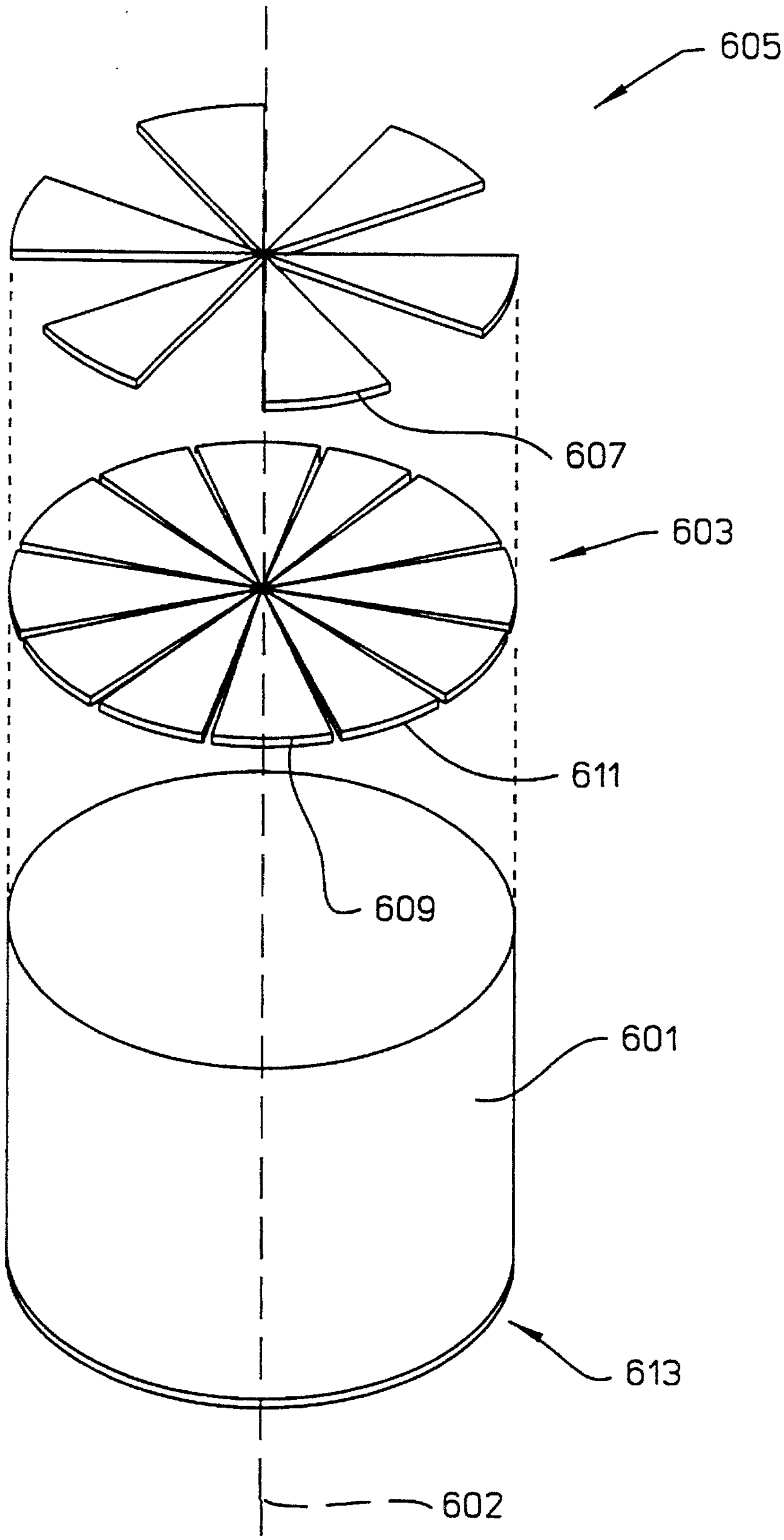
FIGS. 6A through 6D show various views of yet another preferred embodiment of the probe of the invention.

FIG. 6A is an exploded top view of the probe body particularly revealing the first and second sets of electrodes 603, 605. The first set of spaced apart electrodes 603 is coupled with a first surface of the body. The members of the first set of electrodes are spaced apart from one another to provide a respective separation between each pair of adjacent members of the first set. A second set of electrodes 605 is also coupled proximate with the first surface of the body and arranged so that a respective member of the second set substantially overlaps the respective separation between each pair of adjacent members of the first set. For example, in the preferred embodiment shown in FIG. 6A, a member 607 of the second set of electrodes substantially overlaps the separation between a first member 609 and an adjacent second member 611 of the first set of electrodes.

For ease of manufacturing, the second set of electrodes 605 is preferably arranged so that each electrode of the second set substantially overlaps at least a portion of a respective one electrode of the first set. For example, as shown in FIG. 6A, a member 607 of the second set of electrodes substantially overlaps a portion of a first member 609 and a portion of a second member 611 of the first set of electrodes. Preferably a thin insulating layer, for example Mylar film, is disposed between the first and second sets of electrodes. For the sake of simplicity, the thin insulating layer is not shown in the drawings.

Figure 6B:
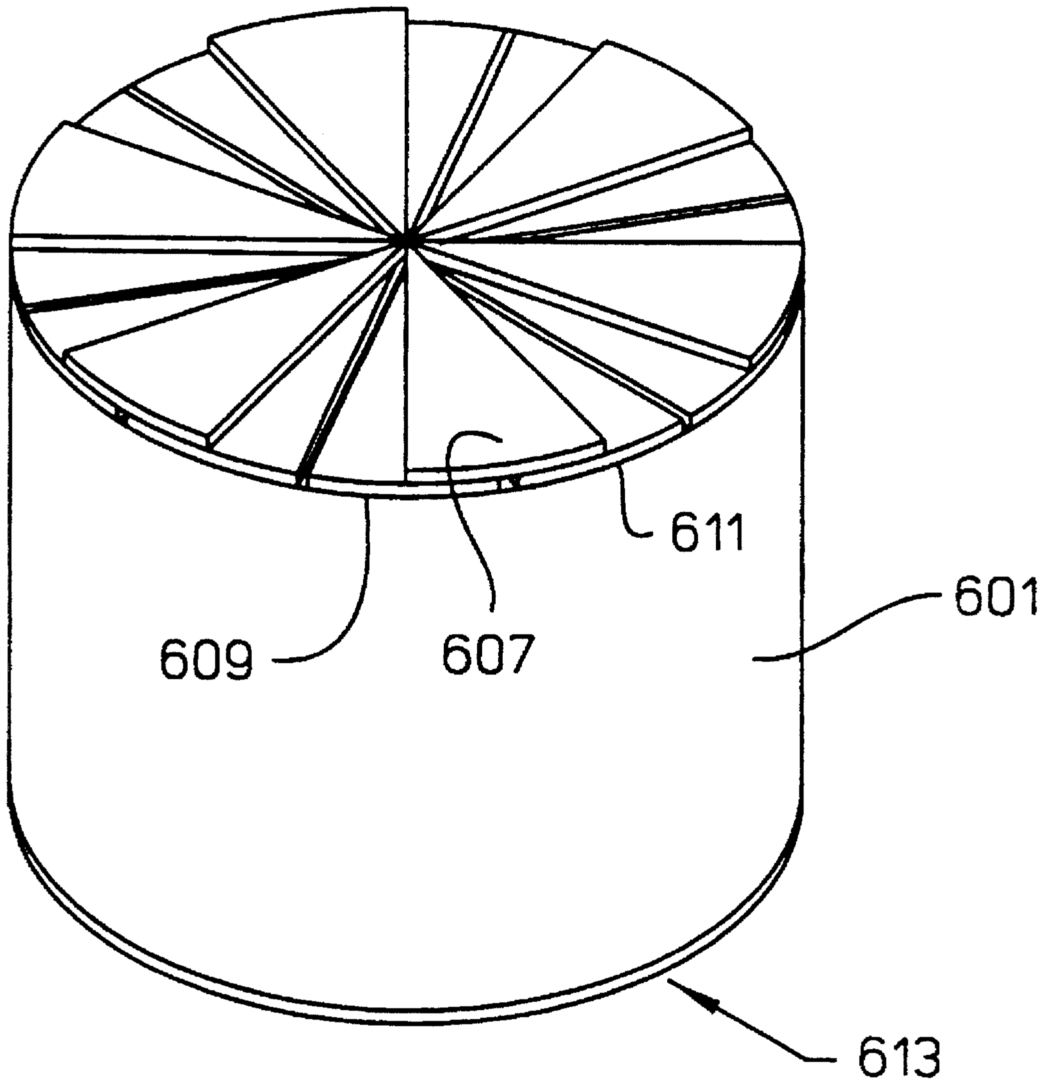
Figure 6C:
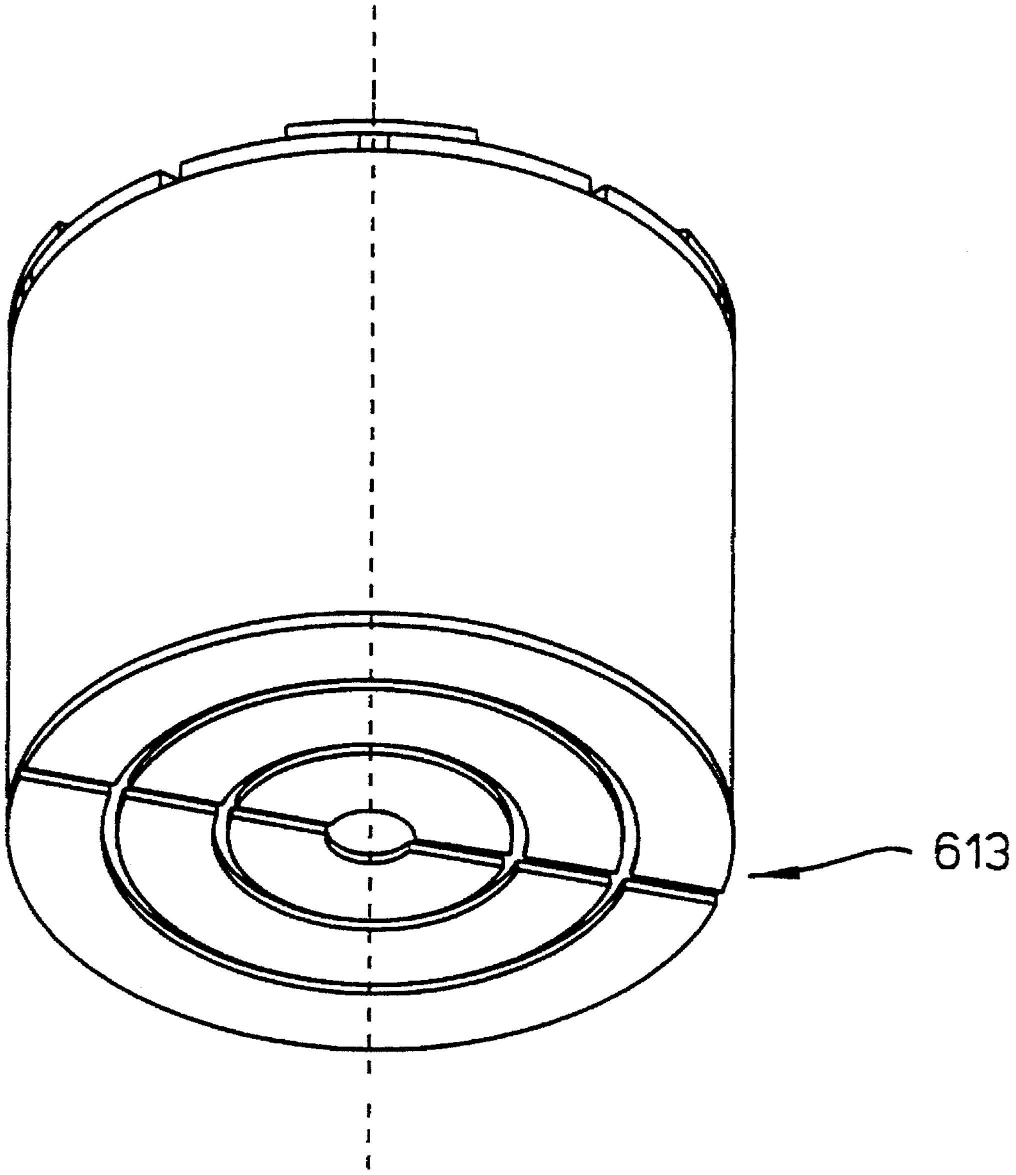
Figure 6D:
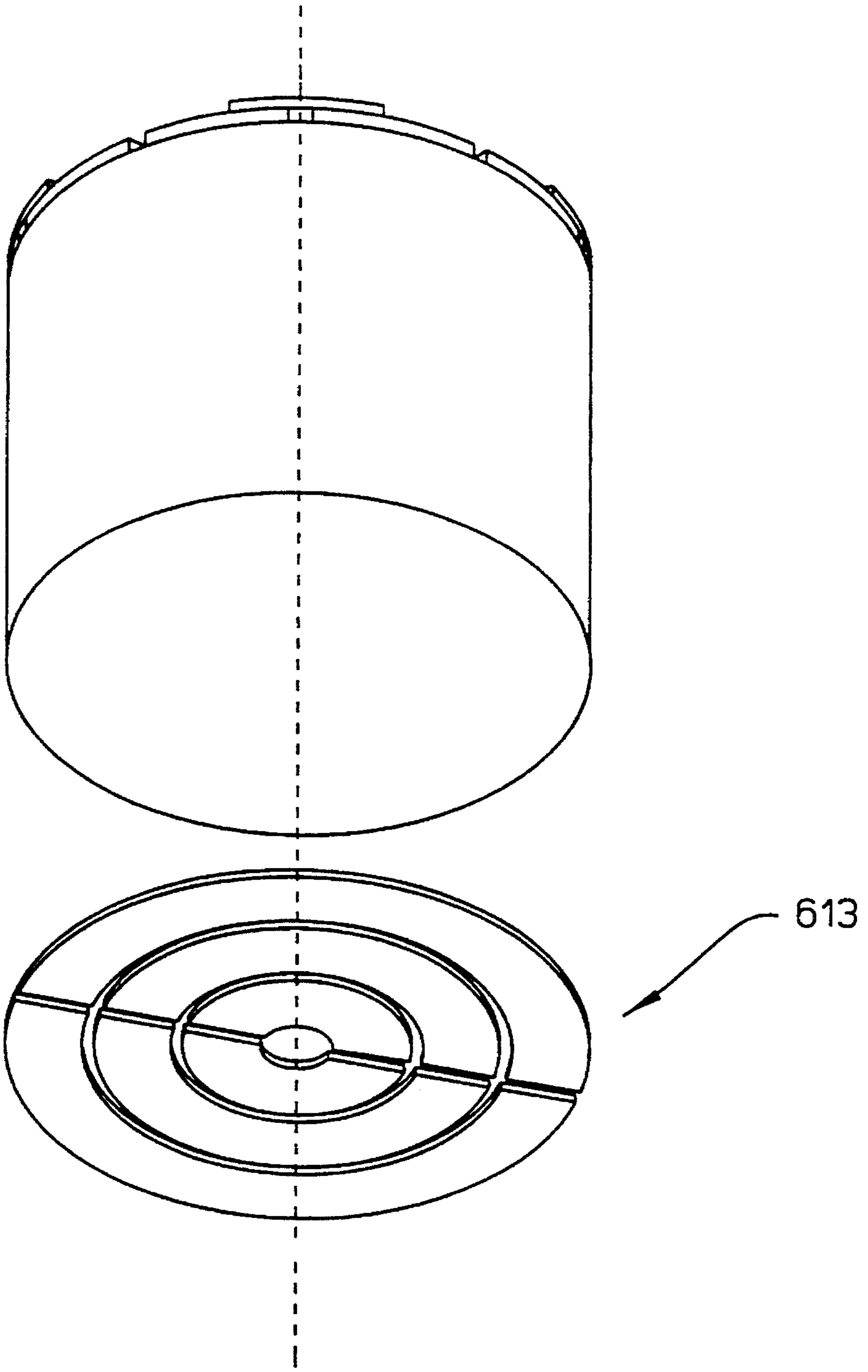

FIG. 6B is a top view of the probe body. FIG. 6C is a bottom view of the probe body. FIG. 6D is an exploded bottom view of the probe body particularly showing the third set of electrodes 613.

Figure 7A:
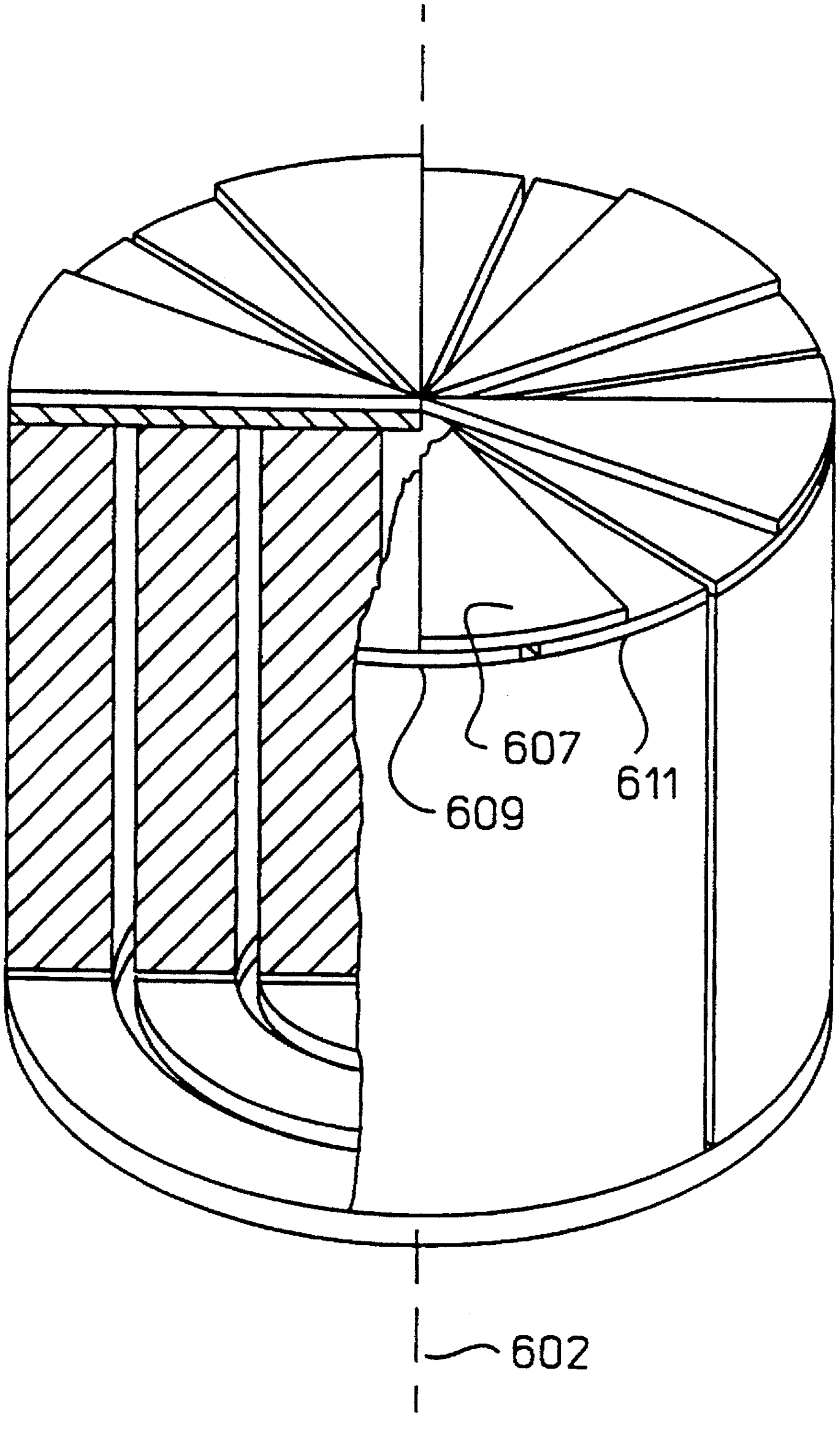
FIGS. 7A, 7B, and 7C are cut away views of the probe body shown in FIGS. 6A through 6D illustrating operation of invention.
Figure 7B:
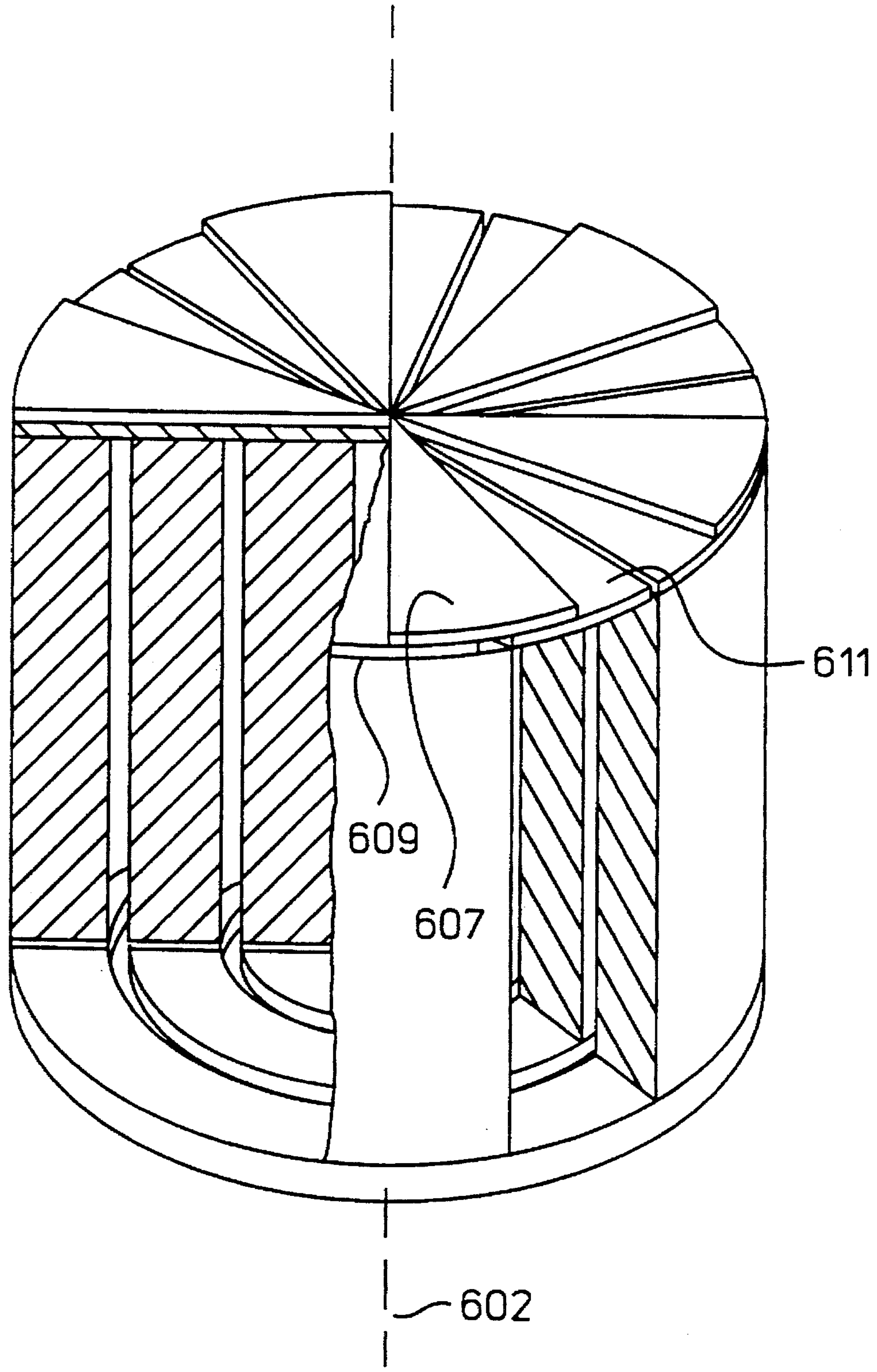
Figure 7C:
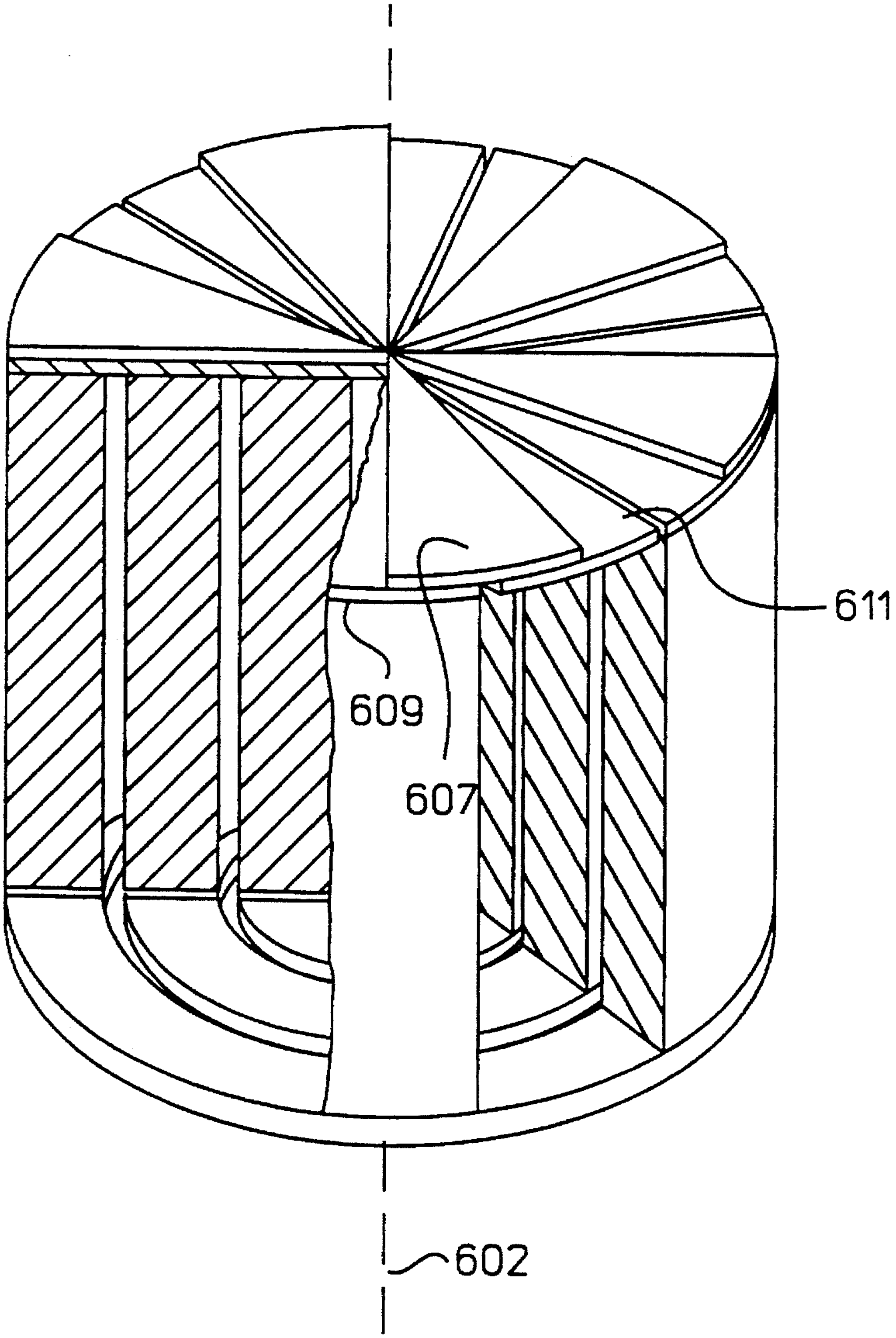

As pointed out previously herein, the relaxor ferroelectric ceramic material becomes polarized and therefore electromechanically active only under influence of the applied bias voltage. The present invention provides a large number of acoustic signal channels by using column regions of the body which are electrically selected by substantially polarizing the regions only when a bias voltage is applied to the regions by the novel electrode arrangement discussed previously herein and illustrated in FIGS. 6A through 6D. FIGS. 7A, 7B, and 7C are cut away views of the probe body shown in FIGS. 6A through 6D illustrating operation of invention.

The electronic switches select all members of the first, second and third set of electrodes, so as to select column regions of the body that are arranged adjacent to one another as shown in FIG. 3A. The bias voltage source coupled with the electronic switches substantially polarizes ceramic material within the selected column regions of the body, while ceramic material in remainder regions of the body is substantially unpolarized. In FIGS. 7A, 7B and 7C the substantially unpolarized regions of the body are cut away to reveal the substantially polarized selected column regions.

The electrode layer switch controller dynamically configures the electronic switches for selectively coupling the bias voltage source to the first and second set of electrodes so as to vary size of the selected polarized regions, as illustrated by FIGS. 7A, 7B, and 7C. For example, for operation of the invention as in FIG. 7A, the third set of electrodes 613 is inductively grounded while the bias voltage source is coupled through the switches to the first and second members 609, 611 of the first set of electrodes and to the member 607 of the second set of electrodes, thereby providing a first row of the polarized column regions extending outwardly from the central axis 602 as shown partially cut away in FIG. 7A. Remaining members of the first and second set of electrodes are similarly configured sequentially about a circumference of the probe to provide a remaining five rows of the polarized column regions extending outwardly from the central axis 602 as shown in FIG. 7A.

The tuned oscillating voltage source excites the selected column regions to emit an acoustic beam having the desired frequency. The beam former variably phases respective oscillating voltages coupled with each of the selected regions so that the acoustic beam scans a medium under examination by the probe. For the sake of simplicity, the medium under examination by the probe and the acoustic; beam are not shown in the figures. Although a plurality of polarized column regions for generating the acoustic waves are shown in FIG. 7A, the polarized column regions are located proximate to one another so that a single effective acoustic aperture is provided. As pointed out previously herein, size of the effective acoustic aperture is based upon size of the polarized column regions.

For FIG. 7B, members of the third set of electrodes 613 are once again inductively grounded while members of the second set of electrodes are once again coupled with the bias voltage source. However for FIG. 7B, alternating members of the first set of electrodes are alternatively biased by coupling to the bias voltage source and unbiased by being substantially disconnected from any bias voltage source. For example, the bias voltage source is coupled through the switches to the first member 609 of the first set of electrodes, while the second member 611 of the first set of electrodes is substantially disconnected from any bias voltage source. In this arrangement the member 607 of the second set of electrodes is also coupled with the bias voltage source, thereby providing a first row of the polarized column regions extending outwardly from the central axis as shown partially cut away in FIG. 7B. Similarly, members of the first and second set of electrodes are configured to provide a remaining five rows of the polarized column regions as shown in FIG. 7B.

As shown, substantially polarized ceramic material is disposed between grounded members of the third set of electrodes and biased members of the first set of electrodes. As additionally shown, substantially polarized ceramic material is disposed between grounded members of the third set of electrodes and where biased members of the second set of electrodes overlap the separation between the pairs of members of the first set of electrodes. Substantially unpolarized remainder regions of the ceramic are shown as cut away.

By comparing FIG. 7B to FIG. 7A, it is seen that the size of the polarized column regions in FIG. 7B is smaller than the size of the column regions in FIG. 7A. Accordingly, it should be understood that size of the effective acoustic aperture corresponding to the polarized column regions shown in FIG. 7B is smaller than the size of the effective acoustic aperture corresponding to the polarized column regions shown in FIG. 7A.

Size of the acoustic aperture is further varied by using the electrode layer switch controller to further vary size of the polarized column regions. For operation of the invention as in FIG. 7C, the third set of electrodes 613 is once again inductively grounded while alternating members of the first set of electrodes are alternatively biased by coupling to the bias voltage source and unbiased by being substantially disconnected from any bias voltage source. For example, the bias voltage source is coupled through the switches to the first member 609 of the first set of electrodes, while the second member 611 of the first set of electrodes is substantially disconnected from any bias voltage source. However, for FIG. 7C the second set of electrodes is unbiased by being substantially disconnected from any bias voltage source, thereby providing a first row of the polarized column regions as shown partially cut away in FIG. 7C.

Similarly, members of the first and second set of electrodes are configured to provide a remaining five rows of the polarized column regions as shown in FIG. 7C. By comparing FIG. 7C to FIGS. 7A and 7C, it is seen that the size of the polarized column regions in FIG. 7C is smaller than the size of the column regions in FIGS. 7A and 7B. Accordingly, it should be understood that size of the effective acoustic aperture corresponding to the polarized column regions shown in FIG. 7B is smaller than the size of the effective acoustic apertures corresponding to the polarized column regions shown in FIGS. 7A and 7B.

The probe of the present invention provides efficient electrical coupling to imaging system components, while further providing variable control over size of the effective acoustic aperture of the probe. Although specific embodiments of the invention have been described and illustrated, the invention is not to be limited to the specific forms or arrangements of parts so described and illustrate, and various modifications and changes can be made without departing from the scope and spirit of the invention. Within the scope of the appended claims, therefore, the invention may be practiced otherwise than as specifically described and illustrated.

What is claimed is:

1. An ultrasonic probe for coupling a beam of acoustic signals between the probe and a medium, the probe comprising:

a body of piezoelectric material, the body having a first surface and an opposing surface;

a first electrode coupled with the first surface of the body;

a second electrode coupled with the first surface of the body and arranged so that the second electrode substantially overlaps the first electrode; and a third electrode coupled with the opposing surface of the body.

2. A probe as in claim 1 further comprising an insulator layer disposed between the first electrode and the second electrode.

3. A probe as in claim 1 further comprising a switch for selectively interconnecting the first electrode and the second electrode.

4. A probe as in claim 1 further comprising:

a first set of electrodes coupled with the first surface of the body;

a second set of electrodes coupled with the first surface of the body and arranged so that each electrode of the second set substantially overlaps at least a respective one electrode of the first set.

5. A probe as in claim 4 wherein the piezoelectric material includes a relaxor ferroelectric ceramic material having a variable polarization.

6. A probe as in claim 5 wherein at least one bias voltage source is coupled with the electrodes for substantially polarizing ceramic material within selected regions of the body.

7. A probe as in claim 6 further comprising switches coupled with the first and second set of electrodes for changing an acoustic aperture of the probe by varying size of the selected polarized regions.

8. A probe as in claim 7 further comprising a means for controlling the switches so as to change the acoustic aperture of the probe in response to transmission of the acoustic beam from the probe and reception of the acoustic beam by the probe.

9. A probe as in claim 7 further comprising means for controlling the polarization of the selected regions of the piezoelectric material so as to variably tune a frequency of the beam of acoustic signals while controlling the acoustic aperture of the probe.

10. A probe as in claim 6 further comprising switches coupled with the first and second set of electrodes for apodizing the acoustic beam by varying size of the selected polarized regions.

11. A probe as in claim 5 wherein:

the body has a central axis;

each member of the first and second sets of electrodes extend radially outward from the central axis of the body.

12. An ultrasonic probe as in claim 5 wherein each member of the first and second set of electrodes is substantially sector shaped.

13. An ultrasonic probe as in claim 5 further comprising a third set of electrodes coupled with the opposing surface of the body and concentrically arranged about the central axis of the body.

14. An ultrasonic probe as in claim 5 further comprising a third set of electrodes coupled with the opposing surface of the body wherein each member of the third set of electrodes is substantially semicircular.

15. An ultrasonic probe as in claim 1 wherein:

the third electrode has a longitudinal dimension extending along a longitudinal dimension of the probe;

the first and second electrodes each have a respective longitudinal dimension arranged substantially perpendicular to that of the third electrode.

16. An ultrasonic probe as in claim 1 wherein:

the third electrode has a longitudinal dimension extending along a longitudinal dimension of the probe;

the first and second electrodes each have a respective longitudinal dimension arranged substantially parallel to that of the third electrode.

17. An ultrasonic probe for coupling a beam of acoustic signals between the probe and a medium, the probe comprising:

a body of piezoelectric material, the body having a first surface and an opposing surface;

a first pair of adjacent electrodes spaced apart to provide a separation therebetween, and coupled with the first surface of the body;

a second electrode coupled with the first surface of the body and arranged so that the second electrode substantially overlaps the separation between the first pair spaced apart electrodes; and a third electrode coupled with the opposing surface of the body.

18. A probe as in claim 17 further comprising:

a first set of spaced apart electrodes coupled with the first surface of the body, members of the first set of electrodes being spaced apart from one another to provide a respective separation between each pair of adjacent members of the first set; and A second set of electrodes coupled proximate with the first surface of the body and arranged so that a respective member of the second set substantially overlaps the respective separation between each pair of adjacent members of the first set.

19. A probe as in claim 17 wherein:

the piezoelectric material includes a relaxor ferroelectric ceramic material having a variable polarization; and the probe further comprises:

at least one bias voltage source coupled with the electrodes for substantially polarizing ceramic material within selected regions of the body; and switches coupled with the first and second set of electrodes for changing an acoustic aperture of the probe by varying size of the selected polarized regions.

20. A probe as in claim 17 wherein:

the body has a central axis;

each member of the first and second sets of electrodes are substantially sector shaped and extend radially outward from the central axis of the body; and the probe further comprises a third set of substantially semicircular electrodes coupled with the opposing surface of the body and concentrically arranged about the central axis of the body.

* * * * *